United States Patent [19]

Syrier

[11] 4,284,820

[45] Aug. 18, 1981

[54] 3,6,6-TRIMETHYLBICYCLO[3.1.0]HEXANE DERIVATIVES AS PYRETHROD INTERMEDIATES

[75] Inventor: Johannes L. M. Syrier, Amsterdam, Netherlands

[73] Assignee: Shell Oil Company, Houston, Tex.

[21] Appl. No.: 189,982

[22] Filed: Sep. 23, 1980

[30] Foreign Application Priority Data

Sep. 28, 1979 [GB] United Kingdom ............... 33836/79

[51] Int. Cl.³ .......................................... C07C 49/443
[52] U.S. Cl. ............................... 568/374; 260/348.54; 568/342; 568/354; 568/445
[58] Field of Search .................................. 568/374, 343

[56] References Cited

U.S. PATENT DOCUMENTS

| | | | |
|---|---|---|---|
| 3,510,510 | 5/1970 | Kropp | 568/374 |
| 3,565,915 | 2/1971 | Matsui et al. | 568/343 |
| 3,686,097 | 8/1972 | Kropp | 568/374 |
| 3,728,372 | 4/1973 | Siddall | 568/343 |
| 4,247,711 | 1/1981 | Verbrugge et al. | 568/374 |

*Primary Examiner*—Natalie Trousof
*Assistant Examiner*—James H. Reamer

[57] ABSTRACT

4-Formyl-3,6,6-trimethylbicyclo[3.1.0]hex-3-ene is oxidized in one vessel by a peroxy acid via 3,4-epoxy-4-formyl-3,6,6-trimethylbicyclo[3.1.0]hexane and 3,4-epoxy-4-formyloxy-3,6,6-trimethylbicyclo[3.1.0]hexane to 3,6,6-trimethyl-3-hydroxybicyclo[3.1.0]hexan-4-one. The four compounds are novel and are intermediates to pyrethroid insecticides.

2 Claims, No Drawings

3,6,6-TRIMETHYLBICYCLO[3.1.0]HEXANE DERIVATIVES AS PYRETHROD INTERMEDIATES

BACKGROUND OF THE INVENTION

1. Field of the Invention

The present invention relates to new 3,6,6-trimethylbicyclo[3.1.0]hexane derivatives and to processes for their preparation. These compounds are useful materials in the preparation of insecticidally active synthetic pyrethroids.

2. Description of the Prior Art

The invention relates to a compound and to a process for its preparation. This compound is a useful intermediate in the preparation of insecticidally active compounds. The latter compounds are of the pyrethrin type and may, therefore, be called "pyrethroids". As these pyrethroids combine exceptionally good insecticidal properties with a very low mammalian toxicity, they are of great interest to the agrochemical industry and considerable effort has been expended in finding economic routes for their production.

The general formula of one class of these pyrethroids described in U.S. Pat. No. 4,024,163 may be represented as follows:

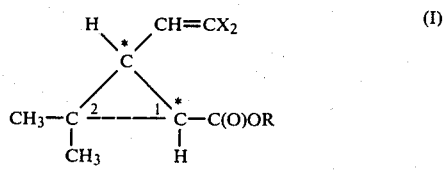

(I)

where each asterisk denotes an asymmetric carbon atom, each X represents a halogen atom and R is a member of a group of radicals known to impart insecticidal activity to the molecule, for example, 3-phenoxybenzyl or alpha-cyano-3-phenoxybenzyl. It is known that for maximum insecticidal activity the acid part of the ester of formula I should be in the (1R,cis) form, i.e. the absolute configuration at carbon atom 1 is R and the two hydrogen atoms on carbon atoms 1 and 3 are in a cis relationship. This nomenclature is known as the Elliott nomenclature and is defined in M. Elliott et al., Nature, 248(1974)710.

It follows, therefore, that if these steroisomeric esters of formula I are to be prepared, either a stereoisomer must be obtained from a racemic form by physical separation techniques. The latter are expensive and laborious and are not readily employed on an industrial scale. In a stereo-specific route the naturally occurring substance (+)-3-carene is used, whose formula is as follows:

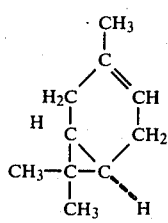

This compound is an inexpensive, readily available natural terpene, which is used as a starting material for the preparation of pyrethroid esters of formula I, via a stereospecific route involving processes disclosed in the present description.

SUMMARY OF THE INVENTION

The invention provides the compound 3,6,6-trimethyl3-hydroxybicyclo[3.1.0]hexan-4-one per se. This compound—also referred to hereinafter as "compound D"—has the following structural formula:

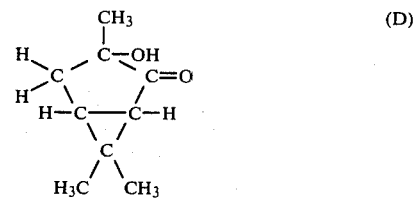

(D)

The invention also provides a process for the preparation of compound D, characterized in that 4-formyl3,6,6-trimethylbicyclo[3.1.0]hex-3-ene—also referred to hereinafter as "compound A"—is epoxidized with formation of 3,4-epoxy-4-formyl-3,6,6-trimethylbicyclo[3.1.0]hexane—also referred to hereinafter as "compound B"—which is oxidized with formation of 3,4-epoxy-4-formyloxy-3,6,6-trimethylbicyclo[3.1.0]hexane—also referred to hereinafter as "compound C"—and the latter compound is oxidized.

Compounds A, B and C have the following structural formulae:

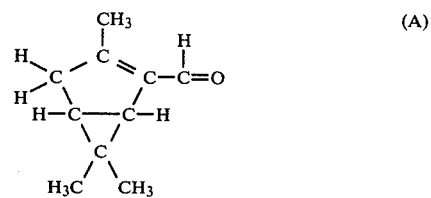

(A)

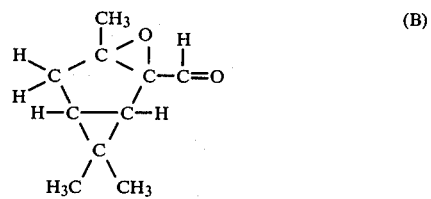

(B)

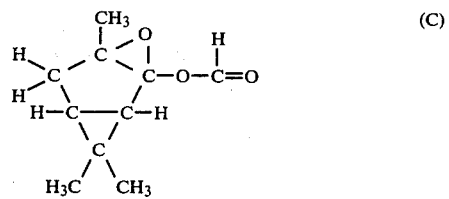

(C)

Compound A may be prepared as described in Chemical Abstracts 71(1969)-123728S. viz. by reacting 2,2-dimethyl-3-(2-oxopropyl)cyclopropylethanal with piperidine in the presence of acetic acid and hydroquinone. The latter aldehyde, in turn, can be prepared as described in British patent application No. 7,913,462.

Compounds B and C are also novel and the invention also provides these two compounds per se. Owing to the presence of two chiral carbon atoms in the cyclopropane ring compounds A, B, C and D exist in two optical isomers (the presence of the other chiral carbon atoms in the molecule being ignored), one having the 1R and the other the 1S configuration. The number 1 indicates the carbon atom of the cyclopropane ring bound to the group —C—C(H)=O (compounds A and B), —C—O—C(H)=O (compound C) and —C=O (compound D). Compounds B and C may have either the 1R or the 1S configuration or they may have a mixture of the two configurations. The 1R configuration of compounds B and C is preferred, because they are precursors to pyrethoids of formula I having the (1R,cis) configuration.

The epoxidation of compound A can be carried out with any suitable epoxidation agent, for example (a) a peroxy acid or (b) hydrogen peroxide in combination with an epoxidation catalyst, (c) an alkyl hydroperoxide, for example, tert-butyl hydroperocide, in combination with an epoxidation catalyst or (d) hydrogen peroxide in combination with a base, for example sodium carbonate. Peroxy acids are preferred, because they rapidly and quantitatively convert compound A with a high selectivity to compound B.

The selectivity to a certain compound, expressed in a percentage, is defined as $$a/b \times 100,$$

wherein "a" is the amount of the starting compound converted into that certain compound and "b" is the amount of converted starting compound.

The oxidation of compound B to compound C is a so-called Baeyer-Villiger oxidation, as described in "Methoden der organischen Chemie" (Houben-Weyl) Book VII/2b (1976) pages 1984–1986, and is suitably carried out with a peroxy acid, thus giving a high yield of compound C.

The invention also provides a process for the preparation of compound D, characterized in that compound C is oxidized or hydrolyzed. This oxidation is also suitably carried out with a peroxy acid and the hydrolysis can be performed in the presence of a base or an acid.

Preferred peroxy acids are an optionally substituted perbenzoic acid (e.g. 3-chloroperbenzoic acid) and peracetic acid. Examples of other suitable peroxy acids are persulphuric acid, perphthalic acid, persuccinic acid and pernonanoic acid.

The processes provided by the invention are suitably carried out in a solvent, for example, dichloromethane, chloroform, carbon tetrachloride, 1,2-dichloroethane, acetone, ethyl acetate, tert-butanol or acetic acid. Very good results have been obtained with chloroform.

According to a preferred embodiment of the present invention the epoxidation of compound A with formation of compound B, the oxidation of compound B with formation of compound C and the oxidation of compound C with formation of compound D are carried out with the aid of a peroxy acid in a single step. This embodiment has the advantage of requiring only one agent for the epoxidation and subsequent oxidations, which are all effected in one reaction zone, without isolation of the intermediate compounds B and C.

The processes provided by the invention are suitably carried out at a temperature in the range of from, for example, 0° C. to 50° C.; an advantage is that these reactions usually proceed very well at a temperature in the range of from 15° C. to 40° C. Ambient temperature, for example, may be used. The above-described one step process is suitably carried out at a molar ratio of peroxy acid to compound A in the range of from 3 to 5, but molar ratios higher than 5 are not precluded.

Compound D can be oxidized with hydrogen peroxide in the presence of an alkali metal hydroxide with formation of 2,2-dimethyl-3-(2-oxopropyl)cyclopropanecarboxylic acid. This acid may be converted as described in, for example, British patent application No. 7,912,133 and its corresponding, copending U.S. Ser. No. 135,405, filed Mar. 31, 1980, for example, by forming the corresponding known alkyl ester of this acid and converting it to the pyrethroid acid (I) using the two-step process described in European Pat. No. 2,849 or using the process described in the earlier mentioned U.S. Pat. No. 4,024,163.

The following Examples further illustrate the invention. Conversions and selectivities were determined by nuclear magnetic resonance (NMR) spectroscopy. The absorptions given are relative to a tetramethylsilane standard and the compounds were dissolved in deuterochloroform. Compounds A, B, C and D all had the 1R configuration. The 3-chloroperbenzoic acid contained about 15%w of 3-chlorobenzoic acid, calculated on 3-chloroperbenzoic acid.

EXAMPLES I–V

A round-bottomed flask provided with a stirrer and placed in a water bath having a temperature between 0° C. and 5° C. was charged with a starting compound and chloroform. Then, 3-chloroperbenzoic acid was gradually added over a period of one hour. The water bath was taken away and stirring was continued for 4 hours, while the temperature was allowed to rise to 20° C. Subsequently, so much dimethyl sulphide was added that all of the peroxides present reacted away and stirring was continued for 30 minutes. Then, the mixture was filtered, the filtrate was washed twice with a saturated aqueous solution of sodium hydrogen carbonate and twice with a 10%w aqueous solution of sodium chloride, the washed solution was dried over anhydrous magnesium sulphate and the solvent was evaporated from the dried solution at a pressure of 2.6 kPa to leave an oily residue.

Table I shows which starting compounds were used and the amounts thereof, the volumes of the chloroform and the amounts of 3-chloroperbenzoic acid and presents the results of five such experiments. An "X" means that the compound could not be detected.

| Example | Starting compound name | amount, mmol | Chloroform ml | 3-chloroperbenzoic acid mmol | Conversion of starting compound, % | Selectivity, % to compound B | C | D |
|---|---|---|---|---|---|---|---|---|
| I | A | 0.80 | 5 | 0.96 | 70 | 30 | 70 | X |
| II | A | 20 | 40 | 40 | 100 | 10 | 80 | 10 |
| III | A | 0.80 | 5 | 2.9 | 100 | X | X | above 90 |
| IV | A | 23.3 | 70 | 93.2 | 100 | X | X | above 90[1] |

| | Starting compound | | | 3-chloroperbenzoic acid | Conversion of starting compound, % | Selectivity, % to compound | | |
|---|---|---|---|---|---|---|---|---|
| Example | name | amount, mmol | Chloroform ml | mmol | | B | C | D |
| V | C | 13.9 | 25 | 20.9 | 95 | X | X | above 90[(2)] |

[(1)]isolated yield 85%
[(2)]isolated yield 90%

The NMR spectra showed the following absorptions:

Compound B

The proton NMR data are as follows:

$\delta$ = 1.01 ppm, singlet, $CH_3$—C—$CH_3$   $\delta$ = 1.09 ppm, singlet, $CH_3$—C—$CH_3$
$\delta$ = 1.47 ppm, singlet, $CH_{CH_3}$—C—O—   $\delta$ = 9.40 ppm, singlet, CH=O
multiplets for $CH_2$—CH—CH

Compound C

The proton NMR data are as follows:

$\delta$ = 1.05 ppm, singlet, $CH_3$—C—$CH_3$   $\delta$ = 1.11 ppm, singlet, $CH_3$—C—$CH_3$
$\delta$ = 1.37 ppm, singlet, $CH_3$—C—O—   $\delta$ = 8.27 ppm, singlet, CH=O
multiplets for $CH_2$—CH—CH The $^{13}C$ NMR data are as follows:

| | $\delta$ (ppm) | | J(Hz) |
|---|---|---|---|
| $CH_3$—C—$CH_3$ | 15.4 | quartet | 129 |
| $CH_3$—C—$CH_3$ | 26.2 | quartet | 126 |
| $CH_3$—C—$CH_3$ | 30.6 | singlet | — |
| $CH_2$—CH | 24.1 | doublet | 170 |
| HC—C(—O)—O— | 33.9 | doublet | 170 |
| $CH_2$—CH | 31.6 | triplet | 129 |
| $CH_2$—C—O | 65.5 | singlet | — |
| $CH_3$—C—O | 14.5 | quartet | 129 |
| HC—C(—O)—O— | 80.3 | singlet | — |
| O—CH | 159.6 | doublet | 230 |

Compound D

The proton NMR data are as follows:
$\delta$ = 1.04 ppm, 1.17 ppm and 1.24 ppm, three singlets for $CH_3$—C—$CH_3$ and $CH_3$—C—OH
$\delta$ = 1.98 ppm, doublet, $\underline{H}$—C—C=O; J = 5 Hz
$\delta$ = 2.2 ppm, doublet of doublet, HC—C$\underline{H}$(H); $J_1$ = 15 Hz, $J_2$ = 6 Hz
$\delta$ = 1.84 ppm, doublet, HC—CH($\underline{H}$); J = 15 Hz
$\delta$ = 1.98 ppm, doublet of doublet, $\underline{H}$C—$CH_2$; $J_1$ = 5 Hz, $J_2$ = 6 Hz variable, broad singlet, —O$\underline{H}$ The $^{13}C$ NMR data are as follows:

| | $\delta$(ppm) | | J(Hz) |
|---|---|---|---|
| $CH_3$—C—$CH_3$ | 17.0 | quartet | 125.6 |
| $CH_3$—C—$CH_3$ | 27.3 | quartet | 125.6 |
| $CH_3$—C—$CH_3$ | 29.3 | singlet | — |
| $CH_2$—CH | 31.6 | doublet | 171.4 |
| HC—C=O | 39.3 | doublet | 173.1 |
| $CH_2$—CH | 35.0 | triplet | 130.7 |
| C—OH | 80.2 | singlet | — |
| $CH_3$—C—OH | 20.5 | quartet | 125.6 |
| C=O | 20.8 | singlet | — |

I claim:

1. 3,6,6-Trimethyl-3-hydroxybicyclo[3.1.0]hexan-4-one.

2. A compound according to claim 1 in the 1R configuration, 1 denoting the carbon atom of the cyclopropane ring bound to the group —C=O.

* * * * *